United States Patent
Woods et al.

(10) Patent No.: US 7,125,422 B2
(45) Date of Patent: Oct. 24, 2006

(54) ACCOMMODATING INTRAOCULAR LENS IMPLANT

(75) Inventors: Randall Woods, Prescott, AZ (US); Robert W. Schulz, St. Helena, CA (US)

(73) Assignee: Quest Vision Technology, Inc., Tiburon, CA (US)

( * ) Notice: Subject to any disclaimer, the term of this patent is extended or adjusted under 35 U.S.C. 154(b) by 0 days.

(21) Appl. No.: 10/280,937

(22) Filed: Oct. 25, 2002

(65) Prior Publication Data

US 2004/0082994 A1    Apr. 29, 2004

(51) Int. Cl.
*A61F 2/14*    (2006.01)
(52) U.S. Cl. .................... 623/6.39; 623/6.34
(58) Field of Classification Search ............... 623/6.39, 623/6.37–6.55, 6.13, 6.34
See application file for complete search history.

(56) References Cited

U.S. PATENT DOCUMENTS

| | | | |
|---|---|---|---|
| 2,834,023 A | 5/1958 | Lieb |
| 3,673,616 A | 7/1972 | Fedorov et al. |
| 3,711,870 A | 1/1973 | Deitrick |
| 3,718,870 A | 2/1973 | Keller |
| 3,866,249 A | 2/1975 | Flom |
| 3,906,551 A | 9/1975 | Otter |
| 3,913,148 A | 10/1975 | Potthast |
| 3,925,825 A | 12/1975 | Richards et al. |
| 4,010,496 A | 3/1977 | Neefe |
| 4,014,049 A | 3/1977 | Richards et al. |
| 4,041,552 A | 8/1977 | Ganias |
| 4,053,953 A | 10/1977 | Flom et al. |
| 4,056,855 A | 11/1977 | Kelman |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,244,060 A | 1/1981 | Hoffer |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,285,072 A | 8/1981 | Morcher et al. |
| 4,298,994 A | 11/1981 | Clayman |
| 4,370,760 A | 2/1983 | Kelman |
| 4,373,218 A | 2/1983 | Schachar |
| 4,409,691 A | 10/1983 | Levy |
| 4,424,597 A | 1/1984 | Schlegel |
| 4,562,600 A | 1/1986 | Ginsberg et al. |
| 4,573,998 A | 3/1986 | Mazzocco |

(Continued)

FOREIGN PATENT DOCUMENTS

CH    681 687 A5    5/1993

(Continued)

*Primary Examiner*—Corrine McDermott
*Assistant Examiner*—William H Matthews
(74) *Attorney, Agent, or Firm*—Advanced Medical Optics, Inc.

(57) ABSTRACT

An improved intraocular lens (42) is provided which more closely mimics the accommodation and focusing of the eye's natural lens. The lens (42) comprises an optic (44) and a flexible, resilient optic positioning element (46) which includes an anterior section (48), a posterior section (50), a bight (56), in cross-section, joining the anterior and posterior sections, and a haptic arm (58) extending between the optic (44) and the optic positioning element (46). The lens (42) may optionally include a posterior optic (44*a*) coupled to the optic positioning element (46). The optic positioning element (46) is formed of unitary construction. The anterior (48) and posterior (50) sections are configured for yieldable engagement with the anterior (52) and posterior (54) walls of the eye capsule (30), respectively.

18 Claims, 5 Drawing Sheets

U.S. PATENT DOCUMENTS

| | | | |
|---|---|---|---|
| 4,615,701 A | 10/1986 | Woods | |
| 4,661,108 A | 4/1987 | Grendahl et al. | |
| 4,664,666 A | 5/1987 | Barrett | |
| 4,693,716 A | 9/1987 | Mackool | |
| 4,710,194 A | 12/1987 | Kelman | |
| 4,737,322 A | 4/1988 | Bruns et al. | |
| 4,790,847 A | 12/1988 | Woods | |
| 4,840,627 A | 6/1989 | Blumenthal | |
| 4,842,601 A | 6/1989 | Smith | |
| 4,888,012 A * | 12/1989 | Horn et al. | 623/6.13 |
| 4,892,543 A * | 1/1990 | Turley | 623/6.13 |
| 4,932,966 A * | 6/1990 | Christie et al. | 623/6.13 |
| 4,932,968 A | 6/1990 | Caldwell et al. | |
| 4,994,082 A | 2/1991 | Richards et al. | |
| 4,994,083 A | 2/1991 | Sulc et al. | |
| 5,047,051 A | 9/1991 | Cumming | |
| 5,171,266 A * | 12/1992 | Wiley et al. | 623/6.22 |
| 5,275,623 A | 1/1994 | Sarfarazi | |
| 5,443,506 A * | 8/1995 | Garabet | 623/6.13 |
| 5,480,428 A * | 1/1996 | Fedorov et al. | 623/6.14 |
| 5,489,302 A | 2/1996 | Skottun | |
| 5,607,472 A * | 3/1997 | Thompson | 623/6.13 |
| 5,674,282 A | 10/1997 | Cumming | |
| 5,776,192 A | 7/1998 | McDonald | |
| 6,117,171 A | 9/2000 | Skottun | |
| 6,152,958 A | 11/2000 | Nordan | |
| 6,176,878 B1 * | 1/2001 | Gwon et al. | 623/6.37 |
| 6,200,342 B1 | 3/2001 | Tassignon | |
| 6,217,612 B1 | 4/2001 | Woods | |
| 6,299,641 B1 | 10/2001 | Woods | |
| 6,322,589 B1 | 11/2001 | Cumming | |
| 6,443,985 B1 * | 9/2002 | Woods | 623/6.46 |
| 6,488,708 B1 * | 12/2002 | Sarfarazi | 623/6.34 |
| 6,503,276 B1 * | 1/2003 | Lang et al. | 623/6.37 |
| 6,524,340 B1 * | 2/2003 | Israel | 623/6.44 |
| 6,551,354 B1 | 4/2003 | Ghazizadeh et al. | |
| 6,558,420 B1 | 5/2003 | Green | |
| 6,592,621 B1 | 7/2003 | Domino | |
| 6,599,317 B1 * | 7/2003 | Weinschenk et al. | 623/6.34 |
| 6,616,691 B1 * | 9/2003 | Tran | 623/6.11 |
| 6,616,692 B1 * | 9/2003 | Glick et al. | 623/6.34 |
| 6,638,305 B1 | 10/2003 | Laguette | |
| 6,660,035 B1 * | 12/2003 | Lang et al. | 623/6.37 |
| 2002/0111678 A1 | 8/2002 | Zadno-Azizi et al. | |
| 2002/0116058 A1* | 8/2002 | Zadno-Azizi et al. | 623/6.37 |
| 2003/0130732 A1 | 7/2003 | Sarfarazi | |
| 2003/0149480 A1* | 8/2003 | Shadduck | 623/6.41 |
| 2003/0187505 A1* | 10/2003 | Liao | 623/6.37 |
| 2003/0204254 A1 | 10/2003 | Peng et al. | |
| 2003/0204255 A1* | 10/2003 | Peng et al. | 623/6.34 |
| 2004/158322 A1 | 8/2004 | Shen | |
| 2004/0181279 A1 | 9/2004 | Nun | |
| 2005/0137703 A1 | 6/2005 | Chen | |

FOREIGN PATENT DOCUMENTS

| | | | | |
|---|---|---|---|---|
| DE | 4038088 | * | 11/1990 | 623/6.37 |
| EP | 0 766 540 B1 | | 8/1999 | |
| WO | WO 99/03427 | * | 1/1999 | 623/6.37 |
| WO | WO 02/19949 A2 | | 3/2002 | |
| WO | WO 02/19949 A3 | | 3/2002 | |
| WO | 2005/018504 A1 | | 3/2005 | |

* cited by examiner

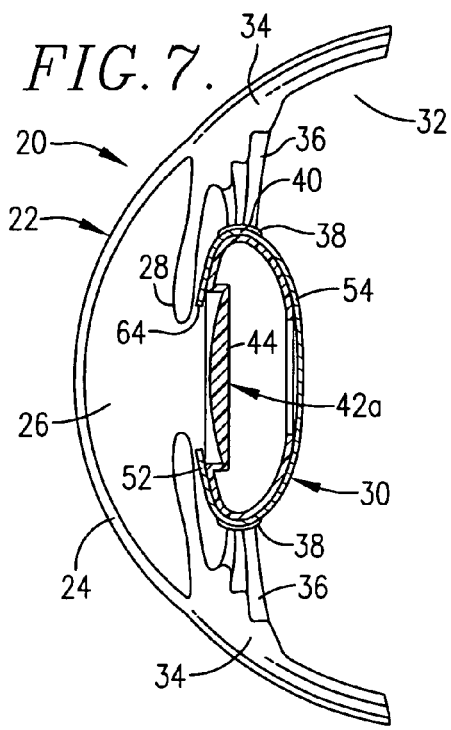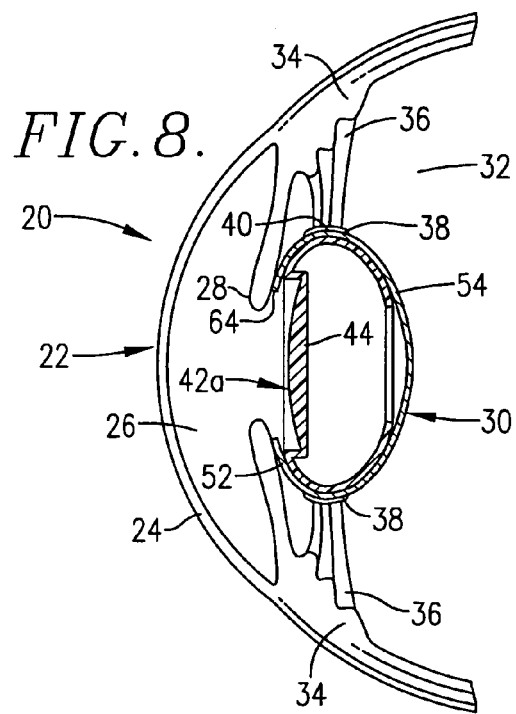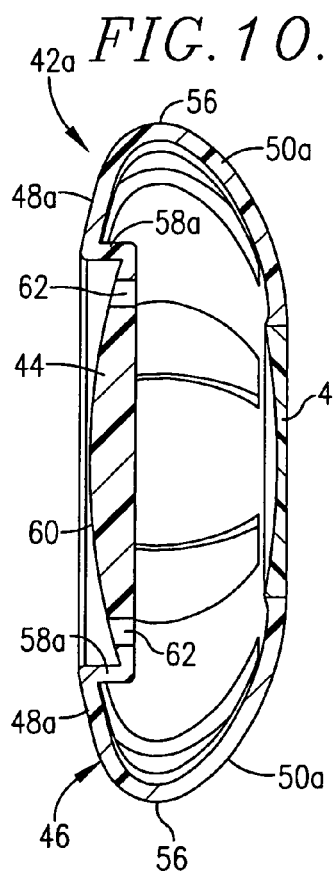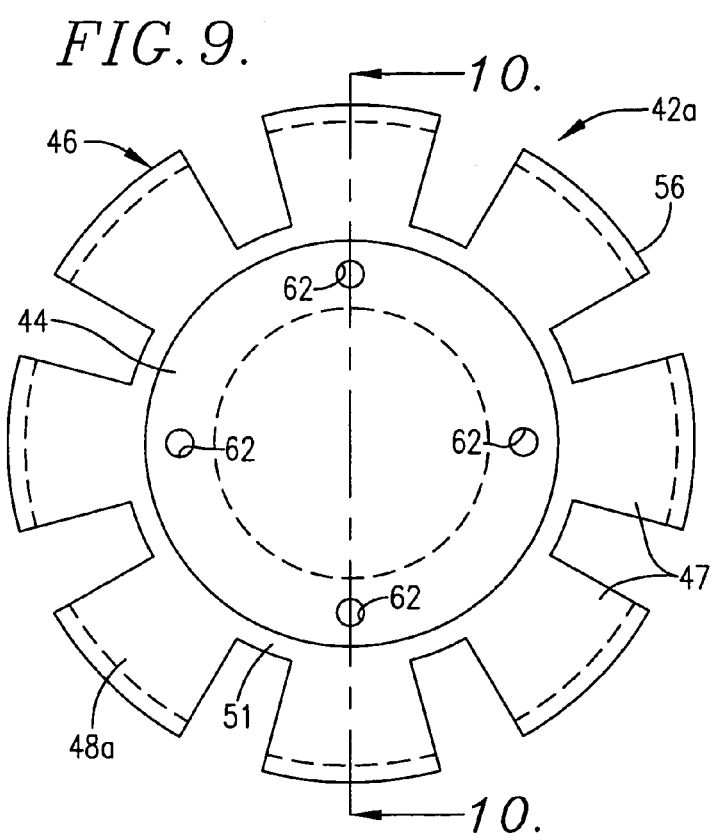

ACCOMMODATING INTRAOCULAR LENS IMPLANT

BACKGROUND OF THE INVENTION

1. Field of the Invention

The present invention relates to accommodating intraocular lenses which can be surgically implanted as a replacement for the natural crystalline lens in the eyes of cataract patients. In particular, lenses of the present invention comprise at least one optic and are capable of being inserted into the natural lens capsule through relatively small incisions in the eye.

2. Description of the Prior Art

Cataracts occur when the crystalline lens of the eye becomes opaque. The cataracts may be in both eyes and, being a progressive condition, may cause fading vision and eventual blindness. Cataracts were once surgically removed along with the anterior wall of the capsule of the eye. The patient then wore eyeglasses or contact lenses which restored vision but did not permit accommodation and gave only limited depth perception.

The first implant of a replacement lens within the eye occurred in 1949 and attempted to locate the replacement lens in the posterior chamber of the eye behind the iris. Problems such as dislocation after implantation forced abandonment of this approach, and for some period thereafter intraocular lenses were implanted in the anterior chamber of the eye.

Others returned to the practice of inserting the lens in the area of the eye posterior to the iris, known as the posterior chamber. This is the area where the patient's natural crystalline lens is located. When the intraocular lens is located in this natural location, substantially normal vision may be restored to the patient and the problems of forward displacement of vitreous humor and retina detachment encountered in anterior chamber intraocular lenses are less likely to occur. Lenses implanted in the posterior chamber are described in U.S. Pat. Nos. 3,718,870, 3,866,249, 3,913,148, 3,925,825, 4,014,552, 4,053,953, and 4,285,072. None of these lenses have focusing capability.

Lenses capable of focusing offered the wearer the closest possible substitute to the natural crystalline lens. U.S. Pat. No. 4,409,691 to Levy is asserted to provide a focusable intraocular lens positioned within the capsule. This lens is located in the posterior area of the capsule and is biased toward the fovea or rear of the eye. The '691 lens is deficient because it requires the ciliary muscle to exert force through the zonules on the capsule in order to compress the haptics inward and drive the optic forward for near vision. However, the ciliary muscles do not exert any force during contraction because the zonules, being flexible filaments, exert only tension, not compression on the capsule. The natural elasticity of the lens causes the capsule to become more spherical upon contraction of the ciliary muscle. Thus there is no inward force exerted on the capsule to compress the haptics of the Levy lens, and therefore accommodate for near vision. Even if such force were somehow available, the Levy lens' haptics are loaded inward when accommodating for near vision. Since accommodation for near vision is the normal status of the capsule, the Levy lens' haptics are loaded, reducing the fatigue life of the springlike haptics.

U.S. Pat. No. 5,674,282 to Cumming is directed towards an accommodating intraocular lens for implanting within the capsule of an eye. The Cumming lens comprises a central optic and two plate haptics which extend radially outward from diametrically opposite sides of the optic and are moveable anteriorly and posteriorly relative to the optic. However, the Cumming lens suffers from the same shortcomings as the Levy lens in that the haptics are biased anteriorly by pressure from the ciliary body. This will eventually lead to pressure necrosis of the ciliary body.

Finally, International Patent Publication WO 01/60286 by Humanoptics AG discloses a two-piece accommodation lens which comprises an optical section positioned within a ring-shaped envelope which is designed to be lodged in the equatorial zone of the lens capsule. However, the envelope and the optical section are not unitarily constructed. The non-unitary construction of the optical section and the envelope that are responsive to ciliary muscle contraction and retraction, results in increased wear and tear of the lens. Thus, the lens may not operate efficiently for a long period of time as is needed for implantation in humans.

There is a need for an intraocular lens implant capable of focusing in a manner similar to the natural lens. The lens should comprise a structure which inhibits the growth of fibrotic tissue and avoids damage to the ciliary body and other eye components. Furthermore, the optic positioning element should preferably be of unitary construction.

SUMMARY OF THE INVENTION

The present invention fills this need by providing an accommodating intraocular lens for implantation substantially within the confines of the capsule of a human eye intermediate the anterior and posterior capsule walls which is safe for long-term use and readily insertable into the eye capsule.

In more detail, the lens of the invention comprises at least one optic presenting opposed anterior and posterior surfaces, coupled with a resilient optic positioning element to cooperatively present a shape that generally conforms to the shape of the capsule. The optic positioning element comprises an anterior section configured for yieldable engagement with the anterior capsule wall, a posterior section configured for yieldable engagement with the posterior capsule wall, a bight, in cross section, joining said anterior and posterior sections, and a haptic arm extending between said optic and said optic positioning element. Another preferred embodiment of the lens of the invention may further comprise a posterior optic also presenting opposed anterior and posterior surfaces coupled to the optic positioning element. Thus, this embodiment comprises an anterior optic and a posterior optic coupled to the optic positioning element in order to accommodate in response to ciliary body movement.

The haptic arm may extend between an optic, preferably the anterior optic if the lens of the invention includes a second posterior optic, as mentioned above, and any one of the three sections which cooperatively make up the optic positioning element. That is, the haptic arm may extend between an optic and the bight, an optic and the anterior section, or an optic and the posterior section.

Preferably, the optic positioning element comprises a plurality of individually continuous, circumferentially spaced apart segments which include anterior and posterior sections and corresponding bights extending therebetween. In preferred embodiments, the individual anterior and posterior sections may be joined by a continuous section presenting an annular orifice therein. The positioning element further comprises at least one and preferably a plurality of haptic arms extending between an optic and the circumferentially spaced apart segments.

The anterior optic for use with the inventive lens preferably presents a convex anterior surface and optionally presents a plurality of circumferentially spaced apart openings therethrough. One of skill in the art should appreciate, however, that the both the anterior and posterior optics may be constructed as either converging or diverging shapes. The optic positioning element is preferably formed of a yieldable synthetic resin material such as a material selected from the group consisting of silicones, acrylates, including polymethylmethacrylates, and mixtures thereof. Even more preferably the optic positioning element is formed of a material having an elastic memory.

BRIEF DESCRIPTION OF THE DRAWINGS

FIG. 7 is a vertical sectional view showing placement, within the capsule of an eye, of a lens of the invention having a haptic arm extending between the anterior section of the optic positioning element and the optic, with the eye focused on an object distant from the viewer.

FIG. 8 is a vertical sectional view showing the location of the lens of FIG. 7 within the capsule of the eye, focused on an object near the viewer.

FIG. 9 is an anterior view of the lens shown in FIG. 7 in its original, non-compressed state.

FIG. 10 is a vertical cross-sectional view of a lens similar to the lens of FIG. 9 taken along line 10—10, but illustrating a posterior optic coupled to the posterior section of the optic positioning element.

DETAILED DESCRIPTION OF THE PREFERRED EMBODIMENTS

Figure 1:
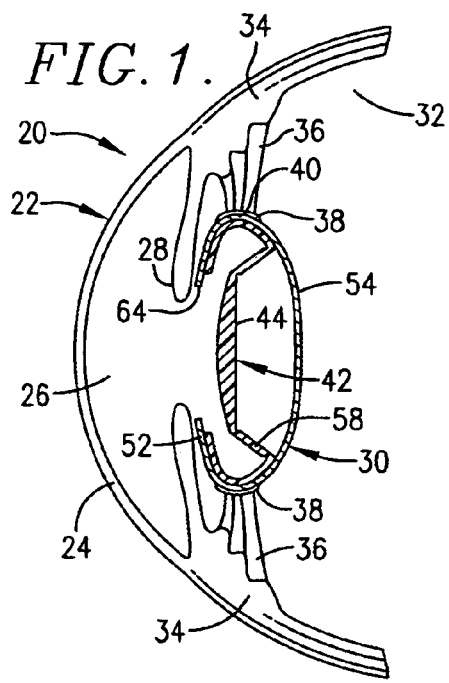
FIG. 1 is a vertical sectional view showing placement, within the capsule of an eye, of a lens of the invention having a haptic arm extending between the posterior section of the optic positioning element and the optic, with the eye focused on an object distant from the viewer.
Figure 2:
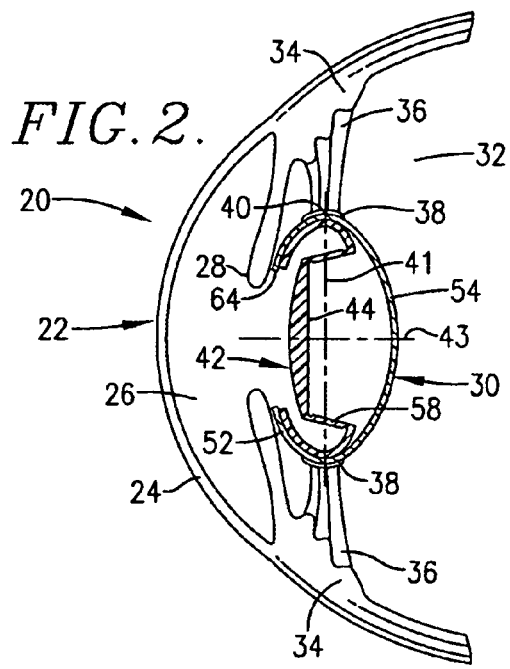
FIG. 2 is a vertical sectional view showing the location of the lens of FIG. 1 within the capsule of the eye, focused on an object near the viewer.

FIGS. 1 and 2 show the various components of the human eye pertinent to this invention. Briefly, the eye 20 includes a frontal portion 22 covered by a cornea 24 which encloses and forms an anterior chamber 26. The anterior chamber 26 contains aqueous fluid and is bounded at the rear by an iris 28. The iris 28 opens and closes to admit appropriate quantities of light into the interior portions of the eye 20. The eye 20 includes a capsule 30 which ordinarily contains the natural crystalline lens. When the eye 20 focuses, the capsule 30 changes shape to appropriately distribute the light admitted through the cornea 24 and the iris 28 to a retina (not shown) at the rearward portion of the eye 20.

The retina is composed of rods and cones which act as light receptors. The retina includes a fovea which is a rodless portion that provides for acute vision. The outside of the rearward or posterior portion 32 of the eye 20 is known as the sclera which joins into and forms a portion of the covering for the optic nerve. Images received by the retina are transmitted through the optic nerve to the brain. The area between the retina and the capsule 30 is occupied by vitreous fluid. The eye 20 further includes a ciliary muscle or body 34 having zonular fibers 36 (also referred to as zonules) which support the capsule 30. The zonular fibers 36 include a layer of elastin tissue 38 which is located substantially about the equatorial portion 40 of the capsule 30.

Ocular adjustments for sharp focusing of objects viewed at different distances is accomplished by the action of the ciliary body 34 on the capsule 30 and the natural crystalline lens (not shown) through the zonular fibers 36. Contraction of the ciliary body 34 compresses the capsule 30 about its equatorial portion 40 causing it to take on a more spherical shape (shown in FIG. 2) for viewing objects that are nearer the viewer. Equatorial portion 40 is located on either side of equatorial axis 41. When the ciliary body 34 retracts and pulls on the zonular fibers 36 to cause the capsule 30 to take on a more discoid shape (shown in FIG. 1), objects at a distance can be viewed in proper focus.

Referring now to FIGS. 1–6, a preferred intraocular lens 42 is shown comprising an optic 44 and a flexible, resilient optic positioning element 46 comprising a plurality of individually continuous, circumferentially spaced apart segments 47 which include anterior and posterior sections 48, 50 which are configured for yieldable engagement with the anterior and posterior capsule walls 52, 54, respectively. When lens 42 is viewed in cross-section, bights 56 join sections 48 and 50. (See FIG. 4) Haptic arms 58 extend between posterior sections 50 and the optic 44, and join the optic 44 and element 46 thereby forming a readily implantable lens.

Figure 4:
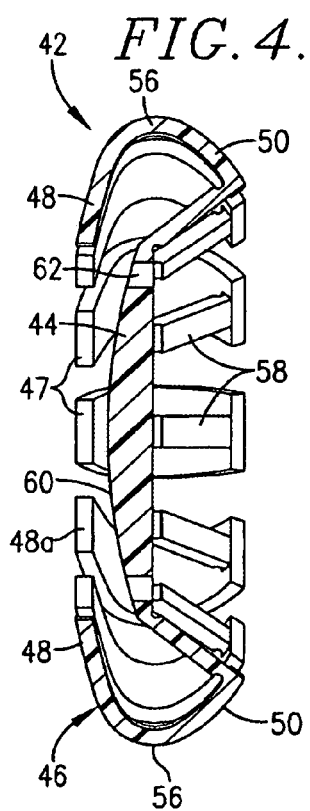
FIG. 4 is a vertical cross-sectional view of the lens of FIG. 3 taken along line 4—4.
Figure 3:
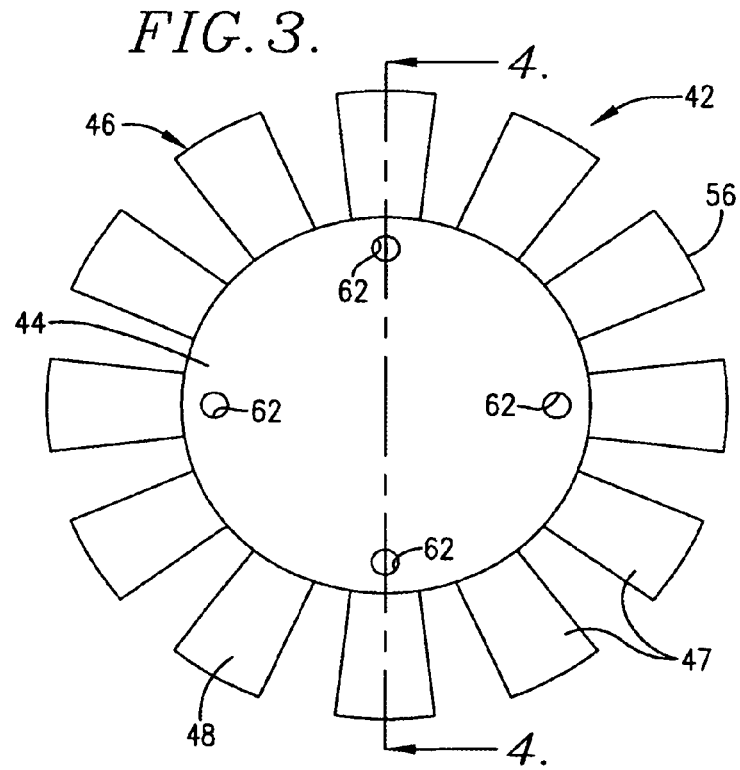
FIG. 3 is an anterior view of the lens shown in FIG. 1 in its original, non-compressed state.
Figure 5:
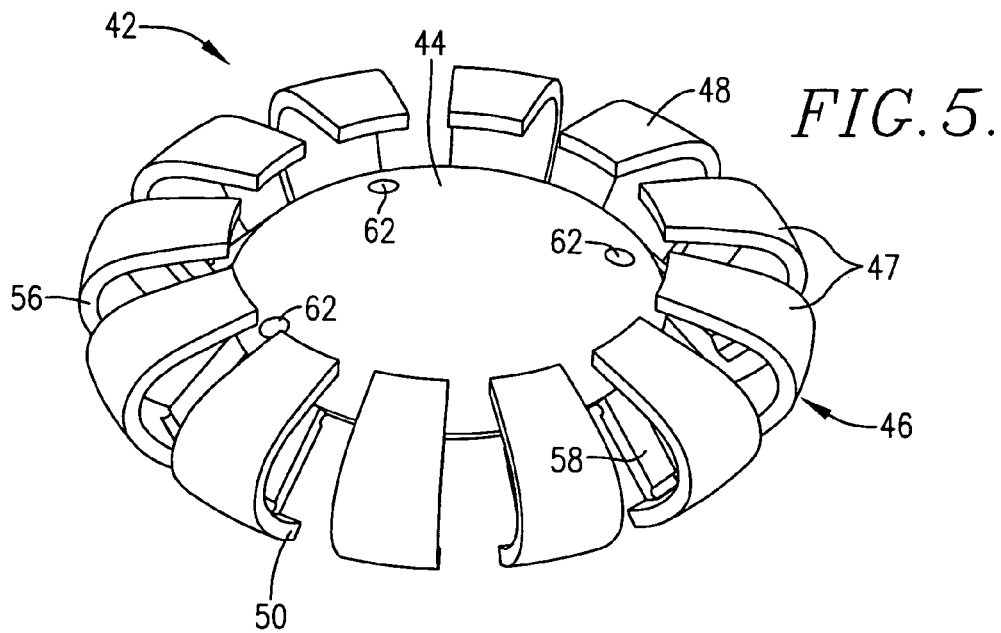
FIG. 5 is an anterior perspective view of the lens of FIG. 1 showing the lens in its original, non-compressed state.
Figure 6:
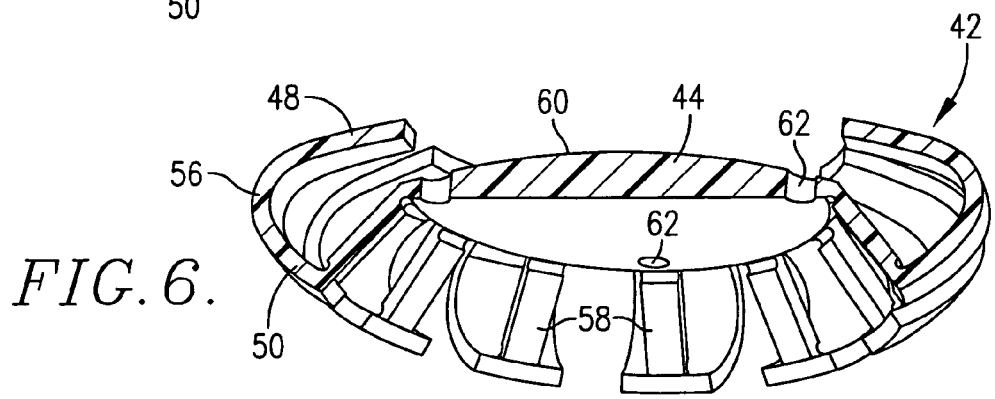
FIG. 6 is a cross-sectional view of the lens of FIG. 5.
Figure 11:
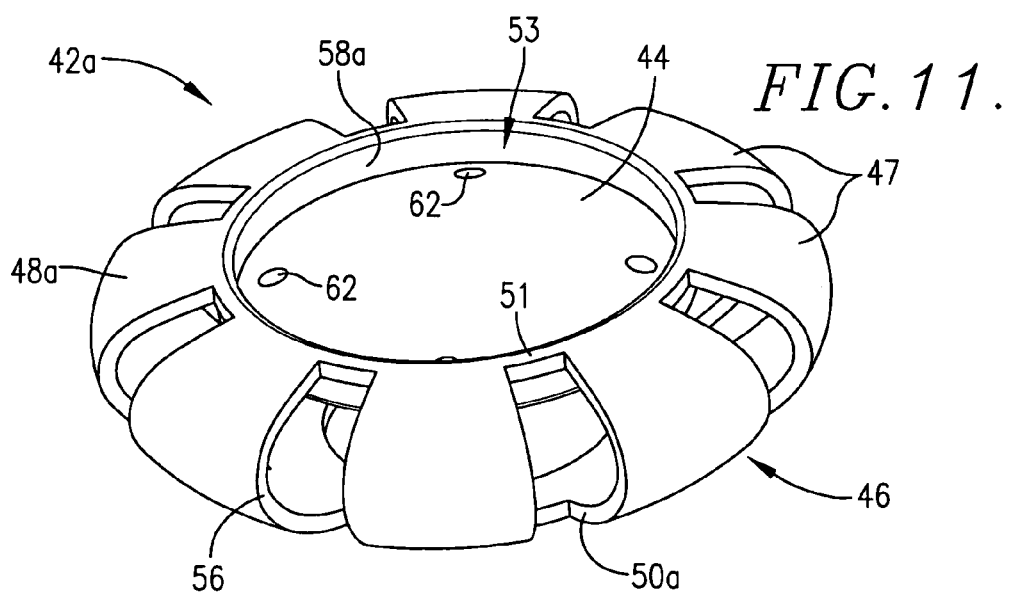
FIG. 11 is an anterior perspective view of the lens of FIG. 7 showing the lens in its original, non-compressed state.
Figure 12:
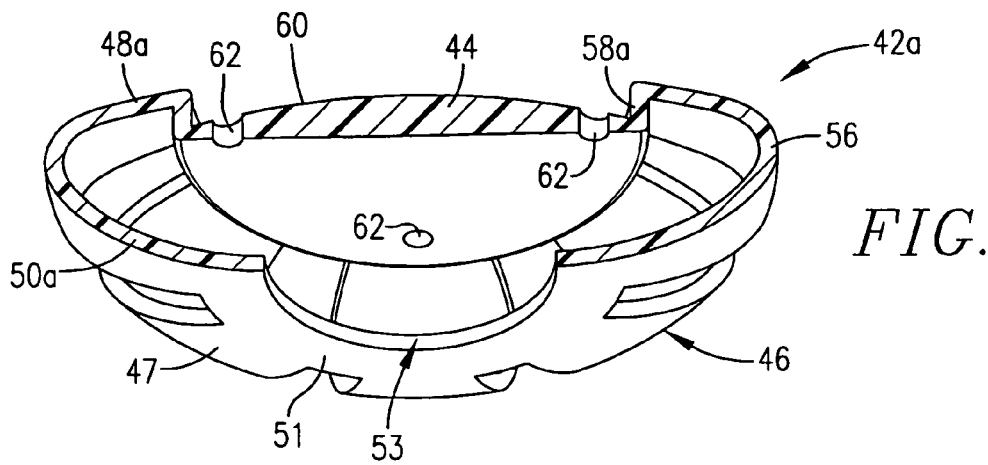
FIG. 12 is a cross-sectional view of the lens of FIG. 11.
Figure 17:
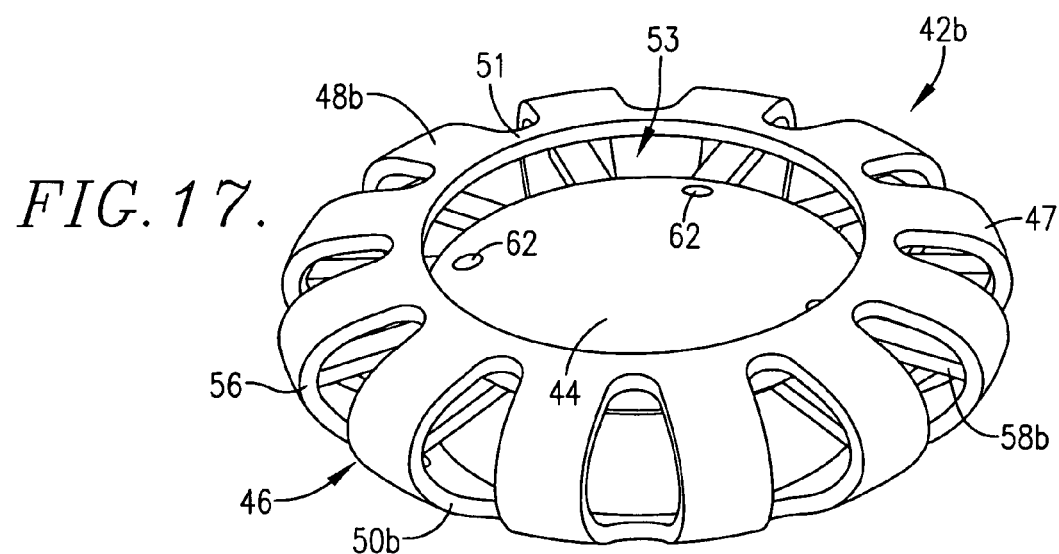
FIG. 17 is an anterior perspective view of the lens of FIG. 13 showing the lens in its original, non-compressed state.
Figure 18:
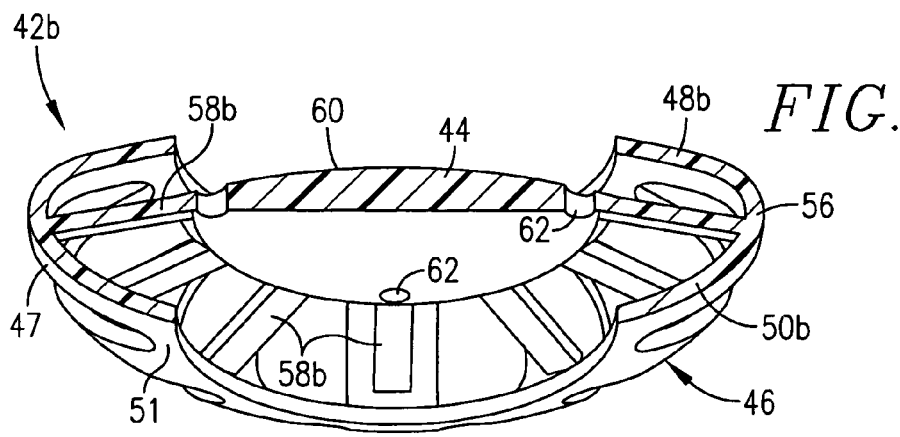
FIG. 18 is a cross-sectional view of the lens of FIG. 17.

As will be apparent from the discussion of further preferred embodiments of the invention below, the embodiment of FIGS. 1–6 is noticeably different in that the anterior and posterior sections 48, 50 are not continuously connected to each other. The anterior and posterior sections 48, 50 are distinct from each other and are individually joined by a plurality of bights 56, as shown in FIG. 4. In this particular embodiment, it is important that the posterior sections 50 not be fixed in position with respect to the posterior capsule wall 54, and this would not be the case if the posterior sections 50 were continuously connected. While not shown in the figures, the anterior sections 48 may be continuously connected.

It will be appreciated from a study of FIGS. 1–6 that the lens 42 is constructed such that the optic 44 thereof is disposed posteriorly relative to at least a portion of the anterior sections 48 of element 46, and within the confines of the positioning element 46. Moreover, the anterior sections 48 present edges or free ends 48a, and the haptic arms 58 orient the entire optic 44 in a posterior, offset relationship relative to at least a portion of the free ends 48a. The edges or free ends 48a also define a central opening oriented about the optical axis of the optic 44, the latter having anterior and posterior directions.

FIGS. 1 and 2 demonstrate accommodation of lens 42 by the eye 20. As shown in FIG. 1, the ciliary body 34 is in a retracted state, thereby stretching the zonular fibers 36 causing the capsule 30 to take on a more discoid configuration. The anterior section, posterior section, and bights 48, 50, and 56, respectively, conform to the shape of the capsule 30 thereby causing the optic 44 to move posteriorly away from the cornea 24 and allowing the eye 20 to focus on objects distant from the viewer. Even more specifically, bights 56 closely conform to the equatorial portion 40 of capsule 30.

As shown in FIG. 2, when the ciliary body 34 contracts, the zonular fibers 36 compress capsule 30 causing it to take on a more spherical configuration. The anterior section and bights 48, 56 remain engaged with the capsule 30, however, the posterior sections 50 shift position relative to the capsule 30 and may disengage the capsule posterior wall 54. The compression of capsule 30, and consequently lens 42, causes the optic 44 to vault anteriorly toward the cornea 24 thus enabling the eye 20 to focus on objects near the viewer.

Another preferred intraocular lens according to the invention is depicted in FIGS. 7–12. Similar to the lens 42 described above, this lens 42a comprises an optic 44 and an optic positioning element 46 including a plurality of circumferentially spaced apart segments 47 which include anterior and posterior sections 48a, 50a. When viewed in cross-section, bights 56 join sections 48a and 50a. A haptic arm 58a extends between optic 44 and anterior section 48a. The haptic arm 58a extends posteriorly from the anterior section 48a to the optic 44. In a further preferred embodiment of the lens 42a, as shown in FIGS. 7–12, the optic 44 may be operably joined to the optic positioning element 46 via a plurality of haptic arms (not shown). The plurality of haptic arms are disposed at various locations about anterior section 48a and extend posteriorly towards the optic 44. Lens 42a is noticeably different from lens 42, illustrated in FIGS. 1–6, in that the plurality of anterior and posterior sections 48a, 50a are continuously attached to each other through continuous sections 51 presenting annular orifices 53 therethrough.

As previously noted, lens 42a may further comprise a posterior optic 44a. FIG. 10 illustrates the lens of FIGS. 7–9 but with a posterior optic 44a coupled to the posterior section 50a of the optic positioning element 46. The posterior optic 44a is illustrated as presenting a concave anterior surface and an opposing planar posterior surface (hereinafter plano-convex). Although the posterior optic 44a is illustrated as plano-concave, any optic shape may be utilized in the manufacture of the intraocular lens of this invention, whether diverging or converging. Examples of converging optic shapes include plano-convex, biconvex, and convex meniscus. Examples of diverging optic shapes include plano-concave, biconcave, and concave meniscus. A concave meniscus optic is a diverging optic having a concave anterior surface wherein the concave surface has a lesser radius of curvature than the opposing convex posterior surface.

FIGS. 7 and 8 demonstrate accommodation of lens 42a by the eye 20. As shown in FIG. 7, when the ciliary body 34 is in the retracted state, the zonular fibers 36 are stretched thereby causing the capsule 30 to take on a more discoid shape. The anterior section, posterior section, and bights 48a, 50a, and 56, respectively, closely conform to the contours of the capsule 30. When in the retracted state, the optic 44 moves posteriorly away from the cornea 24 thereby allowing the eye 20 to focus on objects distant from the viewer.

As shown in FIG. 8, when the ciliary body 34 contracts, the zonular fibers 36 compress capsule 30 causing the capsule 30 to take on a more spherical configuration. The capsule 30 simultaneously compresses element 46 causing lens 42a to acquire a more spherical shape. The anterior section, posterior section, and bights 48a, 50a, and 56, respectively, remain engaged with capsule 30. The compression of element 46 causes the anterior section 48a to move anteriorly toward the cornea 24 thereby causing the optic 44 to shift anteriorly allowing the eye 20 to focus on objects near the viewer.

Figure 16:
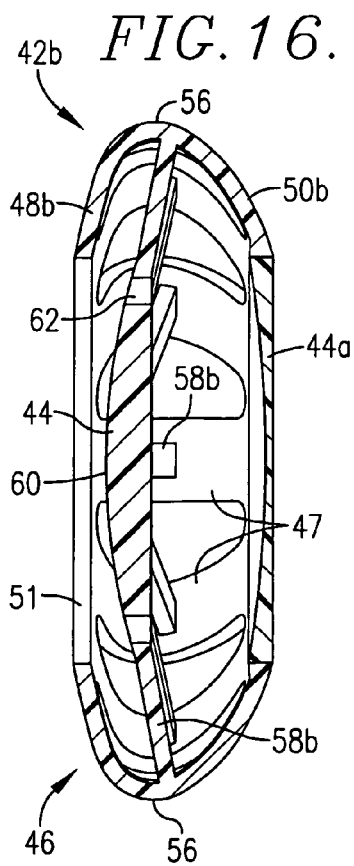
FIG. 16 is a vertical cross-sectional view of a lens similar to the lens of FIG. 15 taken along line 16—16, but illustrating a posterior optic coupled to the posterior section of the optic positioning element.
Figure 15:
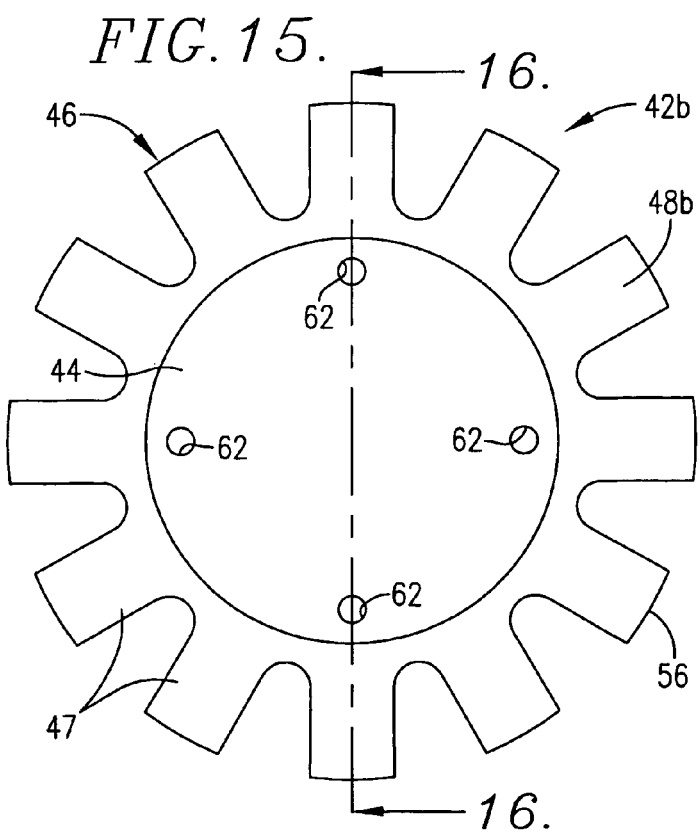
FIG. 15 is an anterior view of the lens shown in FIG. 13 in its original, non-compressed state.

FIGS. 13–18 depict yet another preferred lens 42b according to the invention. As with the lens 42a, shown in FIGS. 7–12, this lens 42b also comprises an optic 44 and an optic positioning element 46 including a plurality of circumferentially spaced apart segments 47 having continuous anterior and posterior sections 48b, 50b, and a bight 56, when viewed in cross-section, joining together the anterior and posterior sections 48b, 50b. In essence, the lens 42b is configured in much the same fashion as the lens 42a of FIGS. 7–12 with the exception that a plurality of haptic arms 58b extend from the bight 56 toward the optic 44. As shown in FIG. 16, when the lens 42b is in its original, non-compressed state, the haptic arms 58b are vaulted slightly toward anterior section 48b.

As with lens 42a, lens 42b is also illustrated as further comprising a posterior optic 44a coupled to the posterior section 50b of the optic positioning element 46. As noted in connection with the discussion of FIG. 10 above, the posterior optic 44a may be constructed as either a diverging or converging optic shape.

Figure 13:
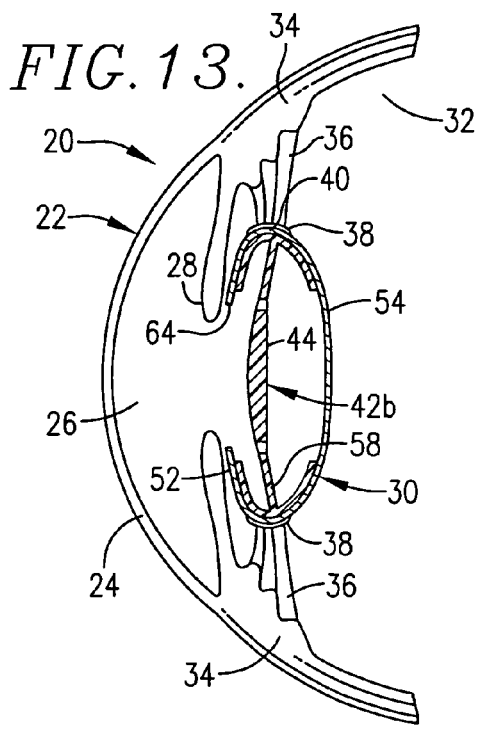
FIG. 13 is a vertical sectional view showing placement, within the capsule of an eye, of a lens of the invention having a haptic arm extending between the bight of the optic positioning element and the optic, with the eye focused on an object distant from the viewer.
Figure 14:
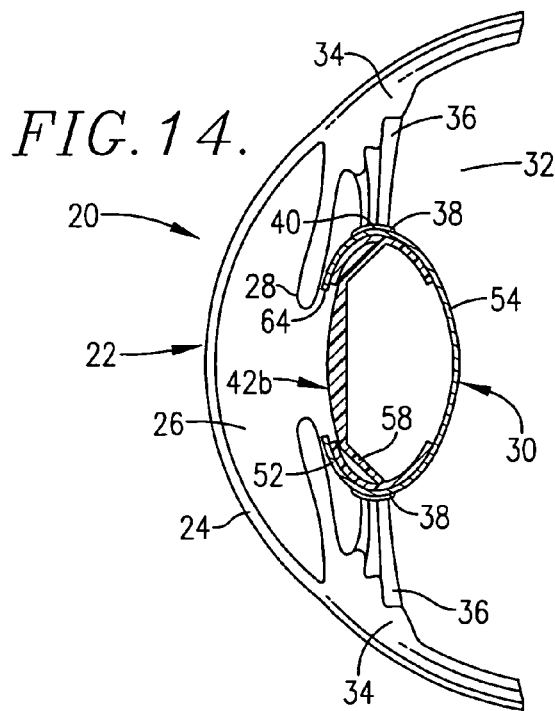
FIG. 14 is a vertical sectional view showing the location of the lens of FIG. 13 within the capsule of the eye, focused on a object near the viewer.

FIGS. 13 and 14 demonstrate accommodation of lens 42b by the eye 20. As shown in FIG. 13, when the ciliary body 34 is in the retracted state, the zonular fibers 36 are stretched thereby causing the capsule 30 to take on a more discoid shape. The anterior section, posterior section, and bight 48b, 50b and 56, respectively, conform to the contours of the capsule 30. When in the retracted state, the optic 44 moves posteriorly away from the cornea 24 thereby allowing the eye 20 to focus on objects distant from the viewer.

As shown in FIG. 14, when the ciliary body 34 contracts, the zonular fibers 36 compress the capsule 30 causing it and lens 42b to take on a more spherical configuration. The anterior section, posterior section, and bight 48b, 50b, and 56, respectively, remain engaged with the capsule 30. The compression of element 46 causes the optic 44 to vault anteriorly toward the cornea 24 allowing the eye 20 to focus on objects near the viewer.

Preferred optics 44 according to the invention may present convex anterior surfaces 60 and may be configured with a plurality of circumferentially spaced openings 62 to allow passage of fluid within the capsule 30 through the optic 44. Preferably, the optic 44 is formed of an acrylic, silicone, similar synthetic resin material, or mixtures thereof.

The optic positioning element 46 is preferably formed of any appropriate biologically inert material conventionally used in intraocular lens construction (e.g., elastic, synthetic resin materials). Examples of suitable lens materials include acrylates (such as polymethylmethacrylates), silicones, and mixtures thereof. It is contemplated that mixtures of silicones and acrylates comprise both chemical mixtures, such as silicone-acrylate blends, and various combinations of silicones and acrylates employed to construct the lens. It is particularly preferred that lenses according to the invention be constructed of a material having an elastic memory (i.e., the material should be capable of substantially recovering its original size and shape after a deforming force has been removed). An example of a preferred material having elastic memory is MEMORYLENS (available from Mentor Ophthalmics in California).

Preferably the inventive lens 42 will have an outer equatorial diameter (distance taken along equatorial axis 41, between outer surfaces of opposing bights 56) of from about 8.5–11 mm, and more preferably about 9.5 mm. Preferably the lens 42 will have a distance between outer surfaces of opposing anterior and posterior sections 48, 50 (taken along optical axis 43) of from about 2–4 mm, and more preferably about 3 mm.

The intraocular lens 42, 42a, 42b of the invention substitutes both locationally and functionally for the original, natural, crystalline lens. Using the lens of FIG. 1 as an example, in order to insert the lens 42 into the capsule 30, an ophthalmic surgeon would remove the natural lens (and thus the cataracts) by conventional methods, leaving an opening 64 in the anterior wall of the capsule 30. Lens 42 is then folded into a compact size for insertion in the capsule 30 through opening 64. Once inserted, the capsule 30 is filled with fluids (e.g., saline solution) which enter the lens 42, causing the lens 42 to return to its original, non-deformed state as shown in FIG. 1. There is no need to suture the lens 42 to the capsule 30 because, due to the size and shape of the lens 42 and conformance of the lens to the capsule walls 22, 32, 40, the lens 42 will not rotate or shift within the capsule 30.

Implantation of the intraocular lens 42, 42a, 42b restores normal vision because, not only does the lens 42 replace the patient's occluded natural lens, but the normal responses of the ciliary body 34 cooperate with the zonular fibers 36 and elastin tissue 38 during focusing of the lens 42. The lens 42 thus follows the eye's natural physiology for focusing to provide a substitute means of optical accommodation. Furthermore, while the foregoing description discloses that the lens 42 could be utilized in cataract patients, the lens 42 may be used in any situation where the natural lens needs to be replaced (e.g., in a patient who wishes to eliminate the need for bifocals).

Optionally, the lens 42, 42a, 42b may be provided with a very thin membrane (not shown) in covering relationship as disclosed in U.S. patent application Ser. No. 09/940,018, filed Aug. 27, 2001, which is incorporated by reference herein. It is contemplated that the membrane would be formed of the same synthetic resin as the optic positioning element 46, but would be much thinner (on the order of a few thousandths of an inch) than the remainder of the element 46. The purpose of the membrane is to prevent or at least impede the passage of migratory cells through openings within the lens 42 and into the inner chamber of the lens 42.

One of ordinary skill in the art will appreciate that the lens 42, 42a, 42b of the present invention may either be formed entirely of unitary construction, or have an optic 44 and an optic positioning element 46 that are constructed separately and interconnected. In either case, the optic positioning element 46 is preferably formed of unitary, integral construction. In any event, each of the embodiments of the lens of the invention comprise an optic 60 which is offset posteriorly in relation to the anterior capsule wall when connected to the optic positioning element 56. One of skill in the art will readily appreciate the optic 60 may be posteriorly offset through various haptic arms 58, 58a, 58b. Thus, in each of these embodiments, the various haptic arms 58, 58a, 58b and optic 44, 60 are preferably disposed entirely within the confines of the optic positioning element 46. Offsetting the optic 60 in this manner eliminates the risk of damaging the iris 28 thereby causing cataracts by preventing contact between the optic 60 and the iris 28 during accommodation. The optic 60 will cause damage to the iris 28 when the optic 60 is not offset posteriorly as described herein. One skilled in the art will readily appreciate the lens 42, 42a, 42b may be positioned within the eye 10, such that the anterior optic 44 faces the retina and the posterior optic 44a faces the cornea 24. When the lens is positioned in this manner, the posterior optic 44a should also be offset to eliminate damage to the iris 28.

The invention claimed is:

1. An accommodating intraocular lens for implantation substantially within the confines of the capsule of a human eye intermediate the anterior and posterior capsule walls, said lens comprising:
    an optic presenting an anterior surface;
    a flexible, resilient optic positioning element coupled to the optic, and comprising—
        a plurality of anterior sections configured for yieldable engagement with the anterior capsule wall,
        a plurality of posterior sections configured for yieldable engagement with the posterior capsule wall,
        a plurality of structures, each structure comprising a bight joining said anterior and posterior sections, and
        a plurality of continuous sections presenting an annular orifice therethrough, the plurality of continuous sections continuously attaching at least one of the plurality of posterior sections and the plurality of anterior sections; and
    a plurality of haptic arms operably coupled with said optic and extending between said optic positioning element and said optic, the entire optic being disposed posteriorly relative to at least a portion of the anterior section.

2. The lens of claim 1, said lens further comprising a posterior optic coupled to said optic positioning element.

3. The lens of claim 1, said optic presenting a convex anterior surface.

4. The lens of claim 1, said optic presenting an opening therethrough.

5. The lens of claim 1, said plurality of continuous sections comprising continuous anterior and posterior sections.

6. The lens of claim 1, said optic positioning element being unitary in construction.

7. The lens of claim 1, said optic positioning element comprising a plurality of bights connecting said anterior and posterior sections.

8. The lens of claim 1, said haptic arms extending between said plurality of anterior sections and said optic.

9. The lens of claim 1, said haptic arms extending between said plurality of posterior sections and said optic.

10. The lens of claim 1, said haptic arms extending between said structure and said optic.

11. The lens of claim 1, said optic positioning element being formed of a yieldable synthetic resin material.

12. The lens of claim 1, said optic positioning element being formed of a material selected from the group consisting of silicones, acrylates, and mixtures thereof.

13. The lens of claim 1, wherein said optic positioning element is formed of a material having an elastic memory.

14. An accommodating lens for implantation substantially within the confines of the capsule of a human eye intermediate the anterior and posterior capsule walls, said lens comprising:
  an optic presenting an anterior surface and comprising an optical axis having an anterior direction and a posterior direction; and
  a flexible, resilient optic positioning element coupled to the optic, and comprising:
    a plurality of anterior sections configured for yieldable engagement with the anterior capsule wall, and
    a plurality of posterior sections configured for yieldable engagement with the posterior capsule wall, and
    a plurality of continuous sections presenting at least an anterior annular orifice therethrough, the plurality of continuous sections continuously attaching at least one of the plurality of posterior sections and the plurality of anterior sections; and
  a plurality of haptic arms operably coupled with said optic such that the entire optic is disposed in the posterior direction relative to the anterior annular orifice.

15. The lens of claim 14, said haptic arm extending between said optic positioning element and said optic.

16. The lens of claim 14, said lens further comprising a posterior optic coupled to said optic positioning element.

17. The lens of claim 14, said optic positioning element being formed of a material selected from the group consisting of silicones, acrylates, and mixtures thereof.

18. An accommodating intraocular lens for implantation substantially within the confines of the capsule of a human eye intermediate the anterior and posterior capsule walls, said lens comprising:
  an optic presenting an anterior surface;
  a flexible, resilient optic positioning element coupled to the optic, and comprising—
    a plurality of anterior sections configured for yieldable engagement with the anterior capsule wall,
    a plurality of posterior sections configured for yieldable engagement with the posterior capsule wall, and
    a plurality of structures, each structure comprising a bright joining said anterior and posterior sections, and
    a plurality of continuous sections presenting at least an anterior annular orifice therethrough, the plurality of continuous sections continuously attaching at least one of the plurality of posterior sections and the plurality of anterior sections; and
  a plurality of haptic arms operably coupled with said optic and extending between said optic positioning element and said optic, said haptic arms orienting the entire optic in a posterior, offset relationship relative to the anterior annular orifice.

* * * * *

UNITED STATES PATENT AND TRADEMARK OFFICE
CERTIFICATE OF CORRECTION

| | | |
|---|---|---|
| PATENT NO. | : 7,125,422 B2 | Page 1 of 1 |
| APPLICATION NO. | : 10/280937 | |
| DATED | : October 24, 2006 | |
| INVENTOR(S) | : Randall Woods and Robert W. Schulz | |

It is certified that error appears in the above-identified patent and that said Letters Patent is hereby corrected as shown below:

Column 8, claim 1 (previous claim 7), line 45, to read: --orly relative to at least a portion of the plurality of anterior sections.--

Column 9, claim 15 (previous claim 20), line 27, to read: --The lens of claim 14, said haptic arms extending--

Signed and Sealed this

Ninth Day of January, 2007

JON W. DUDAS
*Director of the United States Patent and Trademark Office*